United States Patent [19]

Takanabe et al.

[11] 4,185,016
[45] Jan. 22, 1980

[54] PYRROLO BENZODIAZEPINE COMPOUNDS

[75] Inventors: Atuyuki Takanabe; Yoshio Arakawa, both of Hirakata; Yoshio Kagitani, Kashihara; Yasuo Ueda, Hirakata; Daisuke Satoh, Tokushima; Nobuhiko Komatsu, Tokyo, all of Japan

[73] Assignee: The Green Cross Corporation, Osaka, Japan

[21] Appl. No.: 947,418

[22] Filed: Oct. 2, 1978

[30] Foreign Application Priority Data

Dec. 27, 1977 [JP] Japan ................................ 52/156684

[51] Int. Cl.$^2$ ............................................ C07D 487/04
[52] U.S. Cl. ............................. 260/239.3 T; 424/274; 260/239.3 P
[58] Field of Search ............................. 260/239.3 T

[56] References Cited

U.S. PATENT DOCUMENTS

| | | | |
|---|---|---|---|
| 3,523,941 | 8/1970 | Leimgruber et al. | 260/239.3 T |
| 3,524,849 | 8/1970 | Batcho et al. | 260/239.3 T |
| 3,947,408 | 3/1976 | Wright | 260/239.3 T |
| 3,985,732 | 10/1976 | Wright | 260/239.3 T |

FOREIGN PATENT DOCUMENTS 49-32556 8/1974 Japan ................................ 260/239.3 T

OTHER PUBLICATIONS

Kameda et al., "Chem. Pharm. Bull." vol. 16, No. 3, pp. 480–485 (1968).
Chemical Abstracts, vol. 87, (1977) item 135268k, abstracting Scalzo et al., in "Farmaco Ed. Sci.", (1977), (Aug.), vol. 32, No. 5, pp. 579–591.

*Primary Examiner*—Alan L. Rotman
*Assistant Examiner*—Robert T. Bond
*Attorney, Agent, or Firm*—Cushman, Darby & Cushman

[57] ABSTRACT

Novel perhydro-1H-pyrrolo[2,1-C][1,4]benzodiazepin-5-one compounds having antitumor activity, perhydro-1H-pyrrolo[2,1-C][1,4]-benzodiazepin-5,11-dione compounds which are synthetic intermediate of the former, and processes for producing these compounds.

20 Claims, No Drawings

PYRROLO BENZODIAZEPINE COMPOUNDS

This invention relates to novel perhydro-1H-pyrrolo[2,1-C][1,4]-benzodiazepin-5-one compounds having antitumor activity, as well as to perhydro-1H-pyrrolo[2,1-C][1,4]benzodiazepin-5,11-dione compounds which are synthetic intermediate of the former, and to the processes for producing these compounds.

It is disclosed in U.S. Pat. No. 3,361,742 and *J. Am. Chem. Soc.*, 87, 5791–5793 (1965) that 5,10,11,11a-tetrahydro-9,11-dihydroxy-8-methyl-5-oxo-1H-pyrrolo[2,1-C][1,4]-benzodiazepin-2-acrylamide having antitumor and antibacterial activities and represented by the following formula:

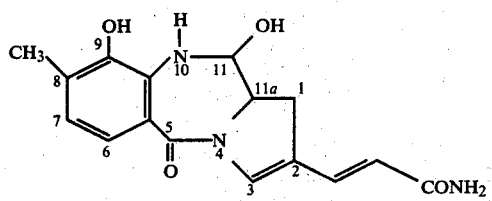

can be produced by cultivating some strains belonging to Genus Streptomyces.

However this compound is produced by biosynthesis, and a number of difficulties are encountered in its production.

In view of above, the present inventors have conducted extensive studies about the derivatives of the compound having the above-mentioned formula to screen out antitumor compounds from them, and searched for novel derivatives chemically synthesizable. As the result, the present inventors have found that novel perhydro-1H-pyrrolo[2,1-C][1,4]benzodiazepin-5-one compounds have antitumor activity and that perhydro-1H-pyrrolo[2,1-C][1,4]benzodiazepin-5,11-dione compounds can be used as synthetic intermediate for the former. Based on these findings, this invention has been accomplished.

It is the object of this invention to provide novel compounds having antitumor activity, their synthetic intermediates and process for their production.

Other objects and advantages of this invention will be apparent from the following descriptions.

According to this invention, there are provided hexahydro-1H-pyrrolo[2,1-C][1,4]benzodiazepin-5-one compounds represented by the following general formula (I):

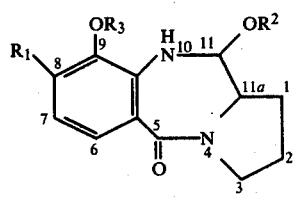

wherein $R_1$ represents hydrogen atom, alkyl group, hydroxy group or alkoxy group, $R_2$ represents hydrogen atom, alkyl group or phenyl-(lower alkyl) group, and $R_3$ represents hydrogen atom or acyl group, as well as tetrahydro-1H-pyrrolo[2,1-C][1,4]benzodiazepin-5-one compounds represented by the following general formula (II):

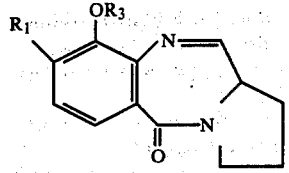

wherein $R_1$ and $R_3$ are as defined above. According to this invention, there are also provided hexahydro-1H-pyrrolo[2,1-C][1,4]benzodiazepin-5,11-dione compounds represented by the following general formula (III):

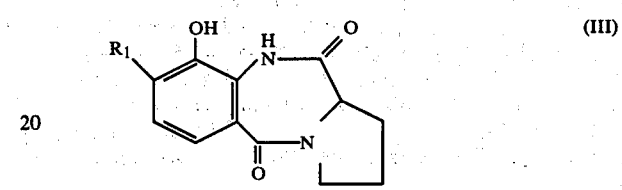

wherein $R_1$ is as defined above, which can be used as synthetic intermediate for the compounds (I) and (II) as mentioned above. According to this invention, there are also provided the processes for producing these compounds.

Concrete examples of the compound of the general formula (I) are listed below:

2,3,5,10,11,11a-hexahydro-9-hydroxy-11-methoxy-8-methyl-1H-pyrrolo[2,1-C][1,4]benzodiazepin-5-one, 2,3,5,10,11,11a-hexahydro-11-ethoxy-9-hydroxy-8-methyl-1H-pyrrolo[2,1-C][1,4]benzodiazepin-5-one, 2,3,5,10,11,11a-hexahydro-9-hydroxy-11-methoxy-1H-pyrrolo-[2,1-C][1,4]benzodiazepin-5-one, 2,3,5,10,11,11a-hexahydro-8,11-dimethoxy-9-hydroxy-1H-pyrrolo[2,1-C][1,4]benzodiazepin-5-one, 2,3,5,10,11,11a-hexahydro-9,11-dihydroxy-8-methyl-1H-pyrrolo[2,1-C][1,4]benzodiazepin-5-one, 2,3,5,10,11,11a-hexahydro-9,11-dihydroxy-1H-pyrrolo[2,1-C][1,4]benzodiazepin-5-one, 2,3,5,10,11,11a-hexahydro-9,11-dihydroxy-8-methoxy-1H-pyrrolo[2,1-C][1,4]benzodiazepin-5-one, 2,3,5,10,11,11a-hexahydro-9-acetoxy-11-methoxy-8-methyl-1H-pyrrolo[2,1-C][1,4]benzodiazepin-5-one, 2,3,5,10,11,11a-hexahydro-9-acetoxy-11-ethoxy-8-methyl-1H-pyrrolo[2,1-C][1,4]benzodiazepin-5-one, 2,3,5,10,11,11a-hexahydro-9-acetoxy-11-hydroxy-8-methyl-1H-pyrrolo[2,1-C][1,4]benzodiazepin-5-one, 2,3,5,10,11,11a-hexahydro-9-acetoxy-11-hydroxy-1H-pyrrolo[2,1-C][1,4]benzodiazepin-5-one, 2,3,5,10,11,11a-hexahydro-9-acetoxy-11-methoxy-1H-pyrrolo[2,1-C][1,4]benzodiazepin-5-one, 2,3,5,10,11,11a-hexahydro-11-ethoxy-9-hydroxy-1H-pyrrolo[2,1-C][1,4]benzodiazepin-5-one, 2,3,5,10,11,11a-hexahydro-9-acetoxy-11-ethoxy-1H-pyrrolo[2,1-C][1,4]benzodiazepin-5-one, 2,3,5,10,11,11a-hexahydro-9-acetoxy-11-hydroxy-8-methoxy-1H-pyrrolo[2,1-C][1,4]benzodiazepin-5-one, 2,3,5,10,11,11a-hexahydro-9-acetoxy-8,11-dimethoxy-1H-pyrrolo[2,1-C][1,4]benzodiazepin-5-one, 2,3,5,10,11,11a-hexahydro-11-ethoxy-9-hydroxy-8-methoxy-1H-pyrrolo[2,1-C][1,4]benzodiazepin-5-one, and 2,3,5,10,11,11a-hexahydro-9-acetoxy-11-ethoxy-8-methoxy-1H-pyrrolo[2,1-C][1,4]benzodiazepin-5-one.

Concrete examples of the compound of the general formula (II) are listed below:

2,3,5,11a-tetrahydro-9-hydroxy-8-methyl-1H-pyrrolo[2,1-C][1,4]benzodiazepin-5-one, 2,3,5,11a-tetrahydro-9-hydroxy-1H-pyrrolo[2,1-C][1,4]benzodiazepin-5-one, 2,3,5,11a-tetrahydro-9-hydroxy-8-methoxy-1H-pyrrolo[2,1-C][1,4]benzodiazepin-5-one, 2,3,5,11a-tetrahydro-9-acetoxy-8-methyl-1H-pyrrolo[2,1-C][1,4]benzodiazepin-5-one, 2,3,5,11a-tetrahydro-9-acetoxy-1H-pyrrolo[2,1-C][1,4]benzodiazein-5-one, and 2,3,5,11a-tetrahydro-9-acetoxy-8-methoxy-1H-pyrrolo[2,1-C][1,4]benzodiazepin-5-one.

Concrete examples of the compound of the general formula (III) are listed below:

2,3,5,10,11,11a-hexahydro-9-hydroxy-8-methyl-1H-pyrrolo[2,1-C][1,4]benzodiazepin-5,11-dione, 2,3,5,10,11,11a-hexahydro-9-hydroxy-1H-pyrrolo[2,1-C][1,4]benzodiazepin-5,11-dione, 2,3,5,10,11,11a-hexahydro-9-hydroxy-8-methoxy-1H-pyrrolo[2,1-C][1,4]benzodiazepin-5,11-dione, and the like.

The compounds represented by the general formula (III), the synthetic intermediate of compounds of the general formula (I) and (II), namely hexahydro-1H-pyrrolo[ 2,1-C][1,4]benzodiazepin-5,11diones, can be synthesized in the following manner.

Thus, they can be produced by subjecting a compound represented by the following general formula (IV) (nitrohydroxybenzoic acid):

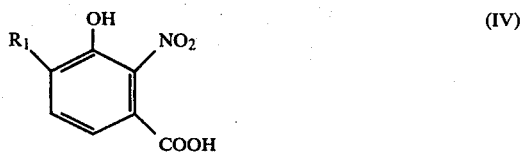

wherein $R_1$ is as defined above, and a compound represented by the following general formula (V) (L-proline ester):

wherein $R_4$ is a lower alkyl group such as methyl, ethyl or the like to a condensation reaction in the medium of nonpolar solvent such as chloroform, methylene chloride, benzene or the like with stirring in the presence of a dehydrating agent such as N,N'-dicyclohexylcarbodiimide, at 0° to 5° C. for 0.5 to 2 hours and then at 5° to 35° C. for 0.5 to 2 hours to obtain a compound represented by the following general formula (VI) (nitrobenzoyl-substituted pyrrolidine):

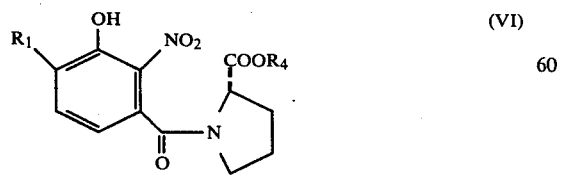

wherein $R_1$ and $R_4$ are as defined above, followed by reducing the latter at ordinary temperature (5° to 35° C.) under ordinary pressure in the medium of alcoholic solvent such as methyl alcohol or ethyl alcohol by the use of platinum catalyst such as platinum oxide, platinum black or the like, palladium catalyst such as palladium-carbon, palladium black or the like, or other metal catalyst such as nickel, copper, zinc or the like to obtain a compound represented by the following general formula (VII) (aminobenzoyl-substituted pyrrolidine):

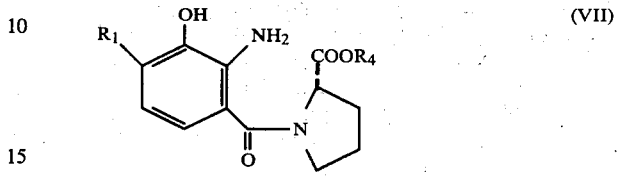

wherein $R_1$ and $R_4$ are as defined above, and finally subjecting the latter to a ring closure reaction by heating a compoud of formula (VII) for a time period of 0.5 to 2.0 hours in the medium of an aromatic solvent such as benzene, toluene, xylene or the like.

Among the compounds represented by formula (I), the compound wherein $R_3$ is hydrogen atom, namely the compounds represented by the following formula (I'):

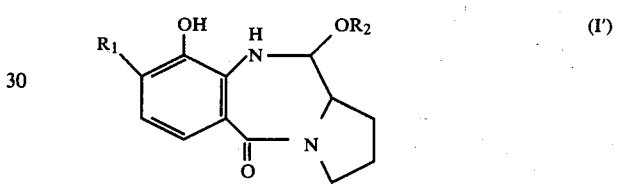

can be produced by reacting a compound of the general formula (III) (hexahydro-1H-pyrrolo[2,1-C][1,4]benzodiazepin-5,11-dione) with a compound represented by the following general formula (benzaldehyde dialkyl acetal):

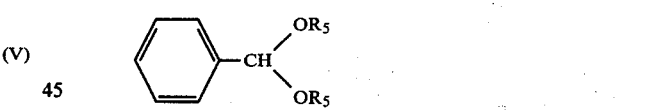

wherein $R_5$ is lower alkyl group such as methyl, ethyl or the like, at 190° to 200° C. for 1 to 3 hours under a stream of nitrogen to obtain a compound represented by the following general formula (VIII) (benzal derivative):

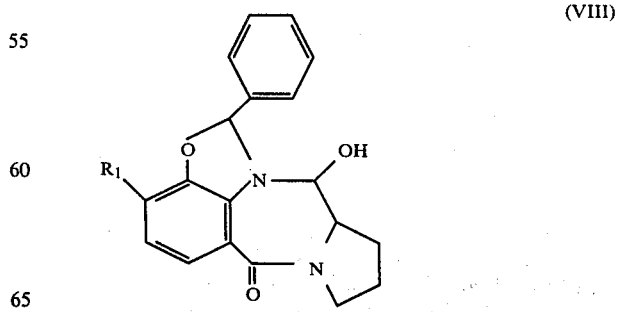

wherein $R_1$ is as defined above, followed by reducing the latter with a complex metal hydride such as lithium aluminum hydride, sodium boron hydride, potassium boron hydride, lithium boron hydride or the like at a temperature of −50° C. to 5° C. to obtain a compound represented by the following general formula (IX) (carbinolamine):

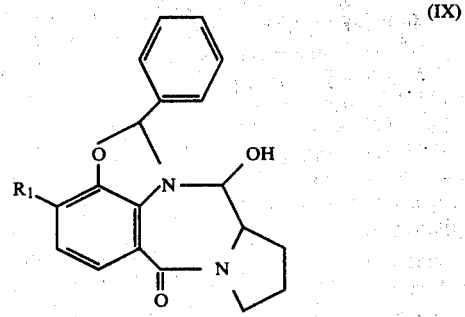

wherein $R_1$ is as defined above, then hydrolyzing the latter with a dilute alcoholic solution of acid at a temperature of 15° to 25° C., dissolving the hydrolyzate into a substance represented by the following general formula (X) (water or alcohols):

$$R_2\text{—OH} \qquad (X)$$

wherein $R_2$ is hydrogen atom, alkyl group or phenyl-(lower alkyl) group, and heating the resulting solution for 0.5 to 1 hour.

Among the compounds represented by formula (I), the compound wherein $R_3$ is acyl group, namely the compounds represented by the following formula (I''):

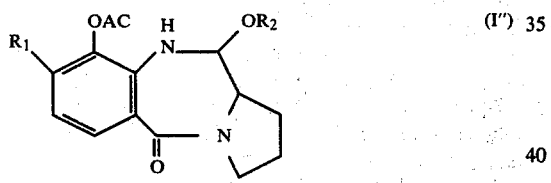

wherein $R_1$ and $R_2$ are as defined above and Ac represents acyl group, can be produced by acylating a compound represented by general formula (I) wherein $R_3$ is hydrogen atom, namely a compound of formula (I'), with an acid anhydride represented by the following general formula:

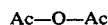

Ac—O—Ac wherein Ac is as defined above, in the presence of a tertiary amine such as triethylamine, pyridine or the like under a stream of nitrogen at a temperature of 0° to 5° C.

The compounds represented by general formula (II):

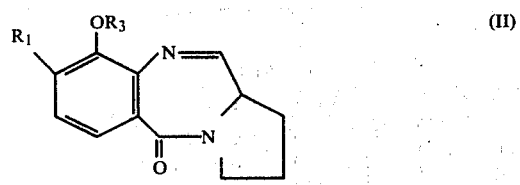

wherein $R_1$ is as defined above and $R_3$ represents hydrogen atom or acyl group, can be produced by heating a compound of formula (I) in the medium of a non-alcoholic solvent such as acetonitrile, benzene, chloroform or the like.

The compounds of general formula (I) can also be produced by mixing a compound of general formula (II) with water or alcohol represented by general formula $R_2$—OH, wherein $R_2$ represents hydrogen atom, alkyl group or phenyl-(lower alkyl) group such as water, methylalcohol or the like, in the presence or absence of the above-mentioned non-alcoholic solvent and allowing the mixture to stand at 5° C. to 35° C. for 1 to 5 hours and then at −10° to −30° C. for 1 to 3 days. The compounds of general formula (II) wherein $R_3$ represents acyl group can also be produced by acylating a compound of general formula (II) wherein $R_3$ is hydrogen atom, in the same manner as above.

In order to confirm the usefulness of the compounds of this invention, the following antitumor activity test and acute toxicity test were carried out.

ANTITUMOR ACTIVITY TEST $CDF_1$ male mice having body weight of 18 to 20 g, 10 heads per one group, were inoculated with $2 \times 10^5$ cells/mouse Leukaemia P388. Twenty four hours after the inoculation, an appointed dose of test compound was intraperitoneally administered to the animals of administration group, after which the administration was repeated for successive 6 days. The survival day numbers of the animals were counted.

Survival time of the animals was expressed by average survival day number. Life-prolongation rate, demonstrating the effect of the compound, was calculated according to the following equation:

$$\text{Life-prolongation rate (\%)} = \frac{\text{Average survival day number of administration group}}{\text{Average survival day number of control (not treatment) group}} \times 100$$

ACUTE TOXICITY TEST:

$LD_{50}$ values of the compounds of this invention were determined by the use of DD strain male mice having body weight of 18 to 20 g, 5 heads per one group. Each test compound was dissolved into physiological solution of sodium chloride containing 1% dimethyl sulfoxide and administered intraperitoneally to the animals. The dose levels were 20 mg/kg, 16.7 mg/kg, 13.9 mg/kg, 11.6 mg/kg and 9.6 mg/kg. One week after the administration, $LD_{50}$ was determined.

The compounds used in the antitumor activity test and the acute toxicity test were the aforementioned novel compounds. The results of tests concerning the compounds of general formula (I) are listed in Table 1, while those concerning the compounds of general formula (II) are listed in Table 2.

Table 1

| Substituent in general formula (I) | | | Antitumor activity | | Acute toxicity | No. of Example illustrating synthesis of the compound |
|---|---|---|---|---|---|---|
| $R_1$ | $R_2$ | $R_3$ | Daily dose (mg/kg) | Life-prolongation rate (%) | $LD_{50}$ (mg/kg) | |
| H | H | H | 5 2.5 | 147.7 125.4 | 12.5 | 14 |

Table 1-continued

| Substituent in general formula (I) | | | Antitumor activity | | Acute toxicity $LD_{50}$ (mg/kg) | No. of Example illustrating synthesis of the compound |
|---|---|---|---|---|---|---|
| $R_1$ | $R_2$ | $R_3$ | Daily dose (mg/kg) | Life-prolongation rate (%) | | |
| H | H | COCH$_3$ | 5 | 145.6 | 12.7 | 23 |
| | | | 2.5 | 123.3 | | |
| H | CH$_3$ | H | 5 | 148.0 | 12.8 | 5, 13 |
| | | | 2.5 | 127.0 | | |
| H | CH$_3$ | COCH$_3$ | 5 | 143.8 | 12.4 | 24, 33 |
| | | | 2.5 | 121.6 | | |
| H | C$_2$H$_5$ | H | 5 | 146.7 | 13.0 | 25 |
| | | | 2.5 | 122.5 | | |
| H | C$_2$H$_5$ | COCH$_3$ | 5 | 143.3 | 13.2 | 26 |
| | | | 2.5 | 121.4 | | |
| CH$_3$ | H | H | 5 | 148.5 | 12.9 | 12 |
| | | | 2.5 | 124.2 | | |
| CH$_3$ | H | COCH$_3$ | 5 | 147.3 | 13.5 | 22 |
| | | | 2.5 | 126.7 | | |
| CH$_3$ | CH$_3$ | H | 5 | 150.0 | 13.8 | 4, 11 |
| | | | 2.5 | 128.4 | | |
| CH$_3$ | CH$_3$ | COCH$_3$ | 5 | 149.0 | 13.9 | 17, 21 |
| | | | 2.5 | 125.0 | | |
| CH$_3$ | C$_2$H$_5$ | H | 5 | 146.5 | 13.3 | 7 |
| | | | 2.5 | 123.3 | | |
| CH$_3$ | C$_2$H$_5$ | COCH$_3$ | 5 | 143.1 | 12.8 | 18 |
| | | | 2.5 | 121.0 | | |
| OCH$_3$ | H | H | 5 | 151.2 | 12.6 | 16 |
| | | | 2.5 | 129.7 | | |
| OCH$_3$ | H | COCH$_3$ | 5 | 149.3 | 12.4 | 27 |
| | | | 2.5 | 123.4 | | |
| OCH$_3$ | CH$_3$ | H | 5 | 147.6 | 12.7 | 15, 6 |
| | | | 2.5 | 121.2 | | |
| OCH$_3$ | CH$_3$ | COCH$_3$ | 5 | 143.3 | 12.3 | 28 |
| | | | 2.5 | 121.1 | | |
| OCH$_3$ | C$_2$H$_5$ | H | 5 | 141.4 | 12.2 | 29 |
| | | | 2.5 | 123.3 | | |
| OCH$_3$ | C$_2$H$_5$ | COCH$_3$ | 5 | 140.5 | 12.7 | 30 |
| | | | 2.5 | 119.7 | | |

Table 2

| Substituent in formula (II) | | Antitumor activity | | Acute toxicity $LD_{50}$ (mg/kg) | No. of Example illustrating synthesis of the compound |
|---|---|---|---|---|---|
| $R_1$ | $R_3$ | Daily dose (mg/kg) | Life-prolongation rate (%) | | |
| H | H | 5 | 152.4 | 13.1 | 9 |
| | | 2.5 | 130.0 | | |
| H | COCH$_3$ | 5 | 149.5 | 13.4 | 31 |
| | | 2.5 | 128.5 | | |
| CH$_3$ | H | 5 | 148.7 | 13.6 | 8 |
| | | 2.5 | 126.7 | | |
| CH$_3$ | COCH$_3$ | 5 | 143.2 | 12.8 | 20, 19 |
| | | 2.5 | 125.0 | | |
| OCH$_3$ | H | 5 | 145.6 | 13.3 | 10 |
| | | 2.5 | 126.7 | | |
| OCH$_3$ | COCH$_3$ | 5 | 140.5 | 13.7 | 32 |
| | | 2.5 | 119.0 | | |

The above-mentioned results of tests demonstrate that the compounds of this invention exhibit an antitumor activity even at a dose as low as 2.5 mg/kg and exhibit a worked antitumor activity at a dose of 5 mg/kg. It is also demonstrated that the compounds of this invention have $LD_{50}$ value of about 12 to 14 mg/kg.

This invention will be illustrated with reference to the following examples which are given in no limitative way.

EXAMPLE 1

16.5 g of L-proline methyl ester and 27.2 g of N,N'-dicyclohexylcarbodiimide were successively added to an ice-cooled and constantly stirred solution of 25.2 g of 3-hydroxy-2-nitro-p-toluic acid dissolved in a mixture consisting of 480 ml of dichloromethane and 43 ml of N,N'-dimethylformamide. The whole mixture was stirred at ice-cooled temperature for 1 hour and then at room temperature for 1 hour. After the reaction, the separated crystalline precipitate was filtered off, and the filtrate was washed with 10% aqueous hydrochloric acid, 5% aqueous solution of sodium hydrogen carbonate and 5% aqueous solution of sodium carbonate. The layer of 5% aqueous solution of sodium carbonate was acidified with hydrochloric acid and extracted with chloroform. The chloroform layer was dehydrated and concentrated. The residue was recrystallized from 50% ethanol, and there was obtained 32.7 g of 1-(3-hydroxy-2-nitro-p-toluyl)-L-proline methyl ester as yellow-colored prismatic crystal having a melting point of 111° to 113.5° C.

IR $v\gamma_{max}^{Nujol}$ cm$^{-1}$: 3250 (OH), 1740, 1630 (C=O).

6.3 g of the 1-(3-hydroxy-2-nitro-p-toluyl)-L-proline methyl ester was dissolved into 120 ml of methanol, to which was added 300 mg of platinum oxide. The ester was catalytically reduced by introducing hydrogen into the solution at ordinary pressure. The catalyst was filtered off from the reaction mixture, and the methanol was distilled off. The residue was suspended in 100 ml of xylene and heated under reflux for 1 hour. After the reaction, the reaction mixture was cooled, and the separated crystalline product was collected by filtration. Using a small quantity of active charcoal, it was recrystallized from methanol to give 4.0 g of 2,3,5,10,11,11a-hexyahydro-9-hydroxy-8-methyl-1H-pyrrolo[2,1-C][1,4]benzodiazepin-5,11-dione of formula (III) as a colorless needle-like crystal having a melting point to 281.5° to 284° C.

Anal. Calcd. for $C_{13}H_{14}N_2O_3$: C 63.40, H 5.73, N 11.38. Found: C 63.46, H 5.73, N 11.37.

| NMR spectrum (D$_6$-DMSO): | |
|---|---|
| 1.76–1.98 | (2H, m), |
| 2.27 | (3H, s), |
| 3.28–3.70 | (4H, m), |
| 4.06 | (1H, AB-q), |
| 7.00 | (1H, d) |
| 7.23 | (1H, d), |
| 9.10–9.40 | (2H, broad). |

IR$\gamma\,_{max}^{Nujol}$ cm$^{-1}$:
3360 (OH, NH), 1695, 1600 (C=0).

EXAMPLE 2

12.9 g of L-proline methyl ester and 21.0 g of N,N'-dicyclohexylcarbodiimide were successively added to an ice-cooled and constantly stirred solution of 18.3 g of 3-hydroxy-2-nitrobenzoic acid dissolved in a mixture consisting of 360 ml of dichloromethane and 30 ml of N,N'-dimethylformamide, and then the same treatment as in Example 1 was carried out. Thus, there was obtained 24.2 g of 1-(3-hydroxy-2-nitrobenzoyl)-L-proline methyl ester as a yellow-colored needle-like crystal having a melting point of 114° to 116° C.

IR $v_{max}^{Nujol}$ cm$^{-1}$: 3230 (OH), 1740, 1640 (C=O).

Then, 6.0 g of the 1-(3-hydroxy-2-nitrobenzoyl)-L-proline methyl ester was treated in the same manner as in Example 1 to give 3.8 g of 2,3,5,10,11,11a-hexahydro-9-hydroxy-1H-pyrrolo[2,1-C][1,4]benzodiazepin-5,11-dione as a colorless needle-like crystal having a melting point of 280° to 282.5° C.

Anal. calcd. for $C_{12}H_{12}N_2O_3$: C 62.06, H 5.21, N 12.06. Found: C 61.97, H 5.20, N 12.12.

IR $\nu_{max}^{Nujol}$ cm$^{-1}$: 3350 (OH, NH), 1690, 1600 (C=O).

EXAMPLE 3

6.5 g of L-proline methyl ester and 10.5 g of N,N'-dicyclohexylcarbodiimide were successively added to an ice-cooled and constantly stirred solution of 10.7 g of 3-hydroxy-4-methoxy-2-nitrobenzoic acid dissolved in a mixture consisting of 180 ml of dichloromethane and 15 ml of N,N'-dimethylformamide, and then the same treatment as in Example 1 was carried out. Thus, there was obtained 12 g of 1-(3-hydroxy-4-methoxy-2-nitrobenzoyl)-L-proline methyl ester as a yellow-colored prismatic crystal having melting point of 108° to 110° C.

IR $\nu_{max}^{Nujol}$ cm$^{-1}$: 3240 (OH), 1740, 1630 (C=O).

Then, 2.0 g of the 1-(3-hydroxy-4-methoxy-2-nitrobenzoyl)-L-proline methyl ester was treated in the same manner as in Example 1 to give 1.3 g of 2,3,5,10,11,11a-hexahydro-9-hydroxy-8-methoxy-1H-pyrrolo[2,1-C][1,4]benzodiazepin-5,11-dione as a colorless needle-like crystal having a melting point of 275° to 277.5° C.

Anal. calcd. for $C_{13}H_{14}N_2O_4$: C 59.54, H 5.38, N 10.68. Found: C 59.66, H 5.35, N 10.61.

IR $\nu_{max}^{Nujol}$ cm$^{-1}$: 3350 (OH, NH), 1695, 1600 (C=O).

EXAMPLE 4

2.0 g of 2,3,5,10,11,11a-hexahydro-9-hydroxy-8-methyl-1H-pyrrolo[2,1-C][1,4]benzodiazepin-5,11-dione was admixed with 300 ml of benzaldehyde dimethyl acetal and heated at 190° to 200° C. for 2 hours with stirring under a stream of nitrogen gas. The liquid reaction mixture was concentrated at 130° to 150° C. under reduced pressure. The concentrate was dissolved in a small quantity of chloroform, passed through a silica gel chromatographic column and eluted with ether. Thus, there was obtained 2.4 g of 6,8,9,10,10a,11-hexahydro-3-methyl-1-phenyl-1H-oxazolo[5,4,3-jk]pyrrolo[2,1-C][1,4]benzodiazepin-6,11-dione as a colorless crystal. Recrystallization of the resulting product from ether gave a colorless needle-like crystal having a melting point of 158.5° to 162.5° C.

IR $\nu max^{Nujol}$ cm$^{-1}$: 1690, 1630 (C=O).

Then, 1.43 g of the 6,8,9,10,10a,11-hexahydro-3-methyl-1-phenyl-1H-oxazolo[5,4,3-jk]pyrrolo[2,1-C][1,4]benzodiazepin-6,11-dione was dissolved in 110 ml of methanol. To the solution, cooled to 0° to 5° C., was slowly added 820 mg of sodium boron hydride with stirring, and the whole mixture was stirred at 0° to 5° C. for 2.5 hours. 800 ml of ethyl acetate and 500 ml of water were added to the reaction mixture, the ethyl acetate layer was separated, and the aqueous layer was extracted with ethyl acetate. The both ethyl acetate layers were combined, dehydrated and concentrated under reduced pressure. The concentrate was dissolved in 375 ml of 2:1 mixture of methyl alcohol and 0.01 N hydrochloric acid and subjected to hydrolyzation at room temperature for 3 hours with stirring. The liquid reaction mixture was extracted with chloroform, the chloroform layer was washed with water and then it was concentrated under reduced pressure at a temperature not exceeding 40° C. The concentrate was dissolved in 50 ml of methanol and heated under reflux for 30 minutes. The reaction mixture was concentrated under reduced pressure at 40° C. or below. The concentrate was dissolved into 4 ml of hot methanol, cooled to −20° C. and allowed to stand at this temperature for 3 days. Thus, 0.35 g of 2,3,5,10,11,11a-hexahydro-9-hydroxy-11-methoxy-8-methyl-1H-pyrrolo[2,1-C][1,4]benzodiazepin-5-one was obtained in a colorless crystalline form. Recrystallization of the resulting product from methanol gave a colorless needle-like crystal having a melting point of 152.5° to 155.5° C.

Anal. calcd. for $C_{14}H_{18}N_2O_3$: C 64.11, H 6.92, N 10.68, Found: C 63.92, H 6.92, N 10.69.

IR $\nu_{max}^{Nujol}$ cm$^{-1}$: 3150 (OH, NH), 1600 (C=O), 1190, 1070 (C—O),

| NMR spectrum (D$_6$-DMSO): | |
|---|---|
| 1.80–2.20 | (4H, m), |
| 2.20 | (3H, S) |
| 3.18 | (3H, S), |
| 3.20–4.00 | (4H, m) |
| 7.16 | (1H, d), |
| 7.20 | (1H, d), |
| 7.70 | (1H, d), |
| 8.65 | (1H, b). |

EXAMPLE 5

1.8 g of 2,3,5,10,11,11a-hexahydro-9-hydroxy-1H-pyrrolo[2,1-C][1,4]benzodiazepin-5,11-dione was treated in the same manner as in Example 4. Thus, 2.2 g of 6,8,9,10,10a,11-hexahydro-1-phenyl-1H-oxazolo[5,4,3-jk]pyrrolo[2,1-C][1,4]benzodiazepin-6,11-dione was obtained in a colorless crystalline form. Recrystallization of the resulting product from ether gave a colorless needle-like crystal having a melting point of 160.5° to 163° C.

IR $\nu_{max}^{Nujol}$ cm$^{-1}$: 1680, 1630 (C=O).

Then, 1.5 g of the 6,8,9,10,10a,11-hexahydro-1-phenyl-1H-oxazolo[5,4,3-jk]pyrrolo[2,1-C][1,4]benzodiazepin-6,11-dione was treated in the same manner as in Example 4. Thus, there was obtained 0.3 g of 2,3,5,10,11,11a-hexahydro-9-hydroxy-11-methoxy-1H-pyrrolo[2,1-C][1,4]benzodiazepin-5-one as a colorless needle-like crystal having a melting point of 150° to 153° C.

Anal. calcd. for $C_{13}H_{16}N_2O_3$: C 62.89, H 6.50, N 11.28. Found: C 62.65, H 6.48, N 11.42.

IR $\nu_{max}^{Nujol}$ cm$^{-1}$: 3150 (OH, NH), 1600 (C=O), 1200, 1080 (C—O).

NMR spectrum (D$_6$-DMSO):

| 1.80–2.25 | (4H, m), |
|---|---|
| 3.18 | (3H, S), |
| 3.25–4.05 | (4H, m), |
| 6.95 | (1H, AB-q), |
| 7.16 | (1H, AB-q), |
| 7.18 | (1H, AB-q), |
| 7.72 | (1H, d), |
| 8.65 | (1H, b). |

EXAMPLE 6

1.0 g of 2,3,5,10,11,11a-hexahydro-9-hydroxy-8-methoxy-1H-pyrrolo[2,1-C][1,4]benzodiazepin-5,11-dione was treated in the same manner as in Example 4. Thus, 1.1 g of 6,8,9,10,10a,11-hexahydro-3-methoxy-1-phenyl-1H-oxazolo[5,4,3-jk]pyrrolo[2,1-C][1,4]benzodiazepin-6,11-dione was obtained in a colorless crystalline form. Recrystallization of the resulting product from ether gave a colorless needle-like crystal having a melting point of 157° to 160.5° C.

IR $\nu_{max}^{Nujol}$ cm$^{-1}$ : 1690, 1630 (C=O).

Then, 1.0 g of the 6,8,9,10,10a,11-hexahydro-3-methoxy-1-phenyl-1H-oxazolo[5,4,3-jk]pyrrolo[2,1-C][1,4]benzodiazepin-6,11-dione was treated in the same manner as in Example 4. Thus, there was obtained 0.2 g of 2,3,5,10,11,11a-hexahydro-8,11-dimethoxy-9-hydroxy-1H-pyrrolo[2,1-C][1,4]benzodiazepin-5-one as a colorless needle-like crystal having a melting pont of 154° to 156° C.

Anal. calcd. for $C_{14}H_{18}N_2O_4$: C 60.42, H 6.52, N 10.07, Found: C 60.26, H 6.51, N 10.25.

IR $\nu_{max}^{Nujol}$ cm$^{-1}$: 3200 (OH, NH), 1600 (C=O), 1210, 1070 (C—O).

NMR spectrum (D$_6$-DMSO):

| 1.80–2.20 | (4H, m), |
|---|---|
| 3.18 | (3H, S), |
| 3.80 | (3H, S), |
| 3.20 –4.05 | (4H, m), |
| 7.16 | (1H, d), |
| 7.20 | (1H, d), |
| 7.74 | (1H, d), |
| 8.66 | (1H, b). |

EXAMPLE 7

350 mg of 6,8,9,10,10a,11-hexahydro-3-methyl-1-phenyl-1H-oxazolo[5,4,3-jk]pyrrolo[2,1-C][1,4]benzodiazepin-6,11-dione was treated in the same manner as in Example 4. The concentrate of the chloroform layer obtained was dissolved in 2 ml of hot ethanol, cooled to −20° C., and allowed to stand at this temperature for 3 days. Thus, 86 mg of 2,3,5,10,11,11a-hexahydro-11-ethoxy-9-hydroxy-8-methyl-1H-pyrrolo[2,1-C][1,4]benzodiazepin-5-one was obtained in a colorless crystalline form. Recrystallization of the resulting product from ethanol gave a colorless needle-like crystal having a melting point of 155° to 157° C.

Anal. calcd. for $C_{15}H_{20}N_2O_3$: C 65.20, H 7.30, N 10.14, Found: C 65.05, H 7.32, N 10.28.

IR $\nu_{max}^{Nujol}$ cm$^{-1}$: 3200 (OH, NH), 1600 (C=O), 1190 (C—O), 1060 (C—O).

EXAMPLE 8

90.4 mg of 2,3,5,10,11,11a-hexahydro-9-hydroxy-11-methoxy-8-methyl-1H-pyrrolo[2,1-C][1,4]benzodiazepin-5-one was dissolved in 15 ml of acetonitrile at an elevated temperature. After dissolution, the solution was concentrated first at ordinary pressure and then under a reduced pressure. The concentrate was dissolved in 1.5 ml of hot benzene, and then 25 ml of n-hexane was added thereto, and the separated precipitate was collected by filtration. This procedure was repeated 2 to 3 times, and there was obtained 63.5 mg of 2,3,5,11a-tetrahydro-9-hydroxy-8-methyl-1H-pyrrolo[2,1-C][1,4]benzodiazepin-5-one as a light yellow powdery product. It had a melting point of 147.5° to 150° C.

Anal. calcd. for $C_{13}H_{14}N_2O_2$: C 67.81, H 6.13, N 12.17. Found: C 67.69, H 6.14, N 12.26.

IR $\nu_{max}^{Nujol}$ cm$^{-1}$: 3260 (OH), 1610 (C=O).

EXAMPLE 9

100 mg of 2,3,5,10,11,11a-hexahydro-9-hydroxy-11-methoxy-1H-pyrrolo[2,1-C][1,4]benzodiazepin-5-one was treated in the same manner as in Example 8. Thus, 62 mg of 2,3,5,11a-tetrahydro-9-hdroxy-1H-pyrrolo[2,1-C][1,4]benzodiazepin-5-one was obtained as a light yellow powdery product having a melting point of 146° to 148.5° C.

IR $\nu_{max}^{Nujol}$ cm$^{-1}$: 3260 (OH), 1605 (C=O).

EXAMPLE 10

100 mg of 2,3,5,10,11,11a-hexahydro-8,11-dimethoxy-9-hydroxy-1H-pyrrolo[2,1-C][1,4]benzodiazepin-5-one was treated in the same manner as in Example 8. Thus, 64 mg of 2,3,5,11a-tetrahydro-9-hydroxy-8-methoxy-1H-pyrrolo[2,1-C] [1,4]benzodiazepin-5-one was obtained as a light yellow powdery product having a melting point of 150° to 153° C.

IR $\nu_{max}^{Nujol}$ cm$^{-1}$: 3250 (OH), 1610 (C=O).

EXAMPLE 11

5.5 mg of 2,3,5,11a-tetrahydro-9-hydroxy-8-methyl-1H-pyrrolo[2,1-C][1,4]benzodiazepin-5-one was dissolved in 0.2 ml of hot methanol and allowed to stand at −20° C. for 3 days. Thus, 3.0 mg of 2,3,5,10,11,11a-hexahydro-9-hydroxy-11-methoxy-8-methyl-1H-pyrrolo[2,1-C][1,4]benzodiazepin-5-one was obtained as a colorless crystal. Its infrared absorption spectrum just coincided with that of the product of Example 4.

EXAMPLE 12

64.4 mg of 2,3,5,11a-tetrahydro-9-hydroxy-8-methyl-1H-pyrrolo[2,1-C][1,4]benzodiazepin-5-one was dissolved in 2.5 ml of hot acetonitrile, 0.5 ml of water was added thereto, and the mixture was allowed to stand first at room temperature for 2 hours and then at −20° C. for 1 day. Thus, 51.1 mg of 2,3,5,10,11,11a-hexahydro-9,11-dihydroxy-8-methyl-1H-pyrrolo[2,1-C][1,4]benzodiazepin-5-one was obtained as a yellow-colored crystal. Recrystallization of the resulting product from aqueous acetonitrile gave a yellow-colored prismatic crystal having a melting point of 154° to 156° C.

Anal. calcd. for $C_{13}H_{16}N_2O_3$: C 62.89, H 6.50, N 11.28. Found: C 62.91, H 6.41, N 11.41.

IR $\nu_{max}^{Nujol}$ cm$^{-1}$: 3350, 2600 (OH, NH), 1585 (C=O).

EXAMPLE 13

20 mg of 2,3,5,11a-tetrahydro-9-hydroxy-1H-pyrrolo[2,1-C][1,4]benzodiazepin-5-one was treated in the same manner as in Example 11. Thus, 11 mg of 2,3,5,10,11,11a-hexahydro-9-hydroxy-11-methoxy-1H-pyrrolo[2,1-C][1,4]benzodiazepin-5-one was obtained as a colorless needle-like crystal having a melting point of 150° to 153° C. Its infrared absorption spectrum just coincided with that of the product of Example 5.

EXAMPLE 14

30 mg of 2,3,5,11a-tetrahydro-9-hydroxy-1H-pyrrolo[2,1-C][1,4]benzodiazepin-5-one was treated in the same manner as in Example 12. Thus, 25 mg of 2,3,5,10,11,11a-hexahydro-9,11-dihydroxy-1H-pyrrolo[2,1-C][1,4]benzodiazepin-5-one was obtained as a yellow-colored prismatic crystal having a melting point of 155° to 157° C.

IR $\nu_{max}^{Nujol}$ cm$^{-1}$: 3350, 2650 (OH, NH), 1590 (C=O).

EXAMPLE 15

15 mg of 2,3,5,11a-tetrahydro-9-hydroxy-8-methoxy-1H-pyrrolo[2,1-C][1,4]benzodiazepin-5-one was treated in the same manner as in Example 11. Thus, 8.5 mg of 2,3,5,10,11,11a-hexahydro-8,11-dimethoxy-9-hydroxy-1H-pyrrolo[2,1-C][1,4]benzodiazepin-5-one was obtained as a colorless needle-like crystal having a melting point of 153.5° to 156° C. Its infrared absorption spectrum just coincided with that of the product of Example 6.

EXAMPLE 16

30 mg of 2,3,5,11a-tetrahydro-9-hydroxy-8-methoxy-1H-pyrrolo[2,1-C][1,4]benzodiazepin-5-one was treated in the same manner as in Example 12. Thus, 26 mg of 2,3,5,10,11,11a-hexahydro-9,11-dihydroxy-8-methoxy-1H-pyrrolo[2,1-C][1,4]benzodiazepin-5-one was obtained as a light yellow prismatic crystal having a melting point of 152° to 155° C.

IR $\nu_{max}^{Nujol}$ cm$^{-1}$: 3330, 2700 (OH, NH), 1585 (C=O).

EXAMPLE 17

49.3 mg of 2,3,5,10,11,11a-hexahydro-9-hydroxy-11-methoxy-8-methyl-1H-pyrrolo[2,1-C][1,4]benzodiazepin-5-one was suspended in 0.5 ml of 1:1 mixture of triethylamine and acetic anhydride and stirred at 0° to 5° C. for 15 minutes under a stream of nitrogen gas. Thus, 30 mg of 2,3,5,10,11,11a-hexahydro-9-acetoxy-11-methoxy-8-methyl-1H-pyrrolo[2,1-C][1,4]benzodiazepin-5-one was obtained as a colorless powdery product. Recrystallization of the resulting product from acetone-ligroin gave a colorless needle-like crystal having a melting point of 147° to 149.5° C.

Anal. calcd. for $C_{16}H_{20}N_2O_4$: C 63.14, H 6.62, N 9.20. Found: C 62.93, H 6.68, N 9.15.

Ir $\nu_{max}^{Nujol}$ cm$^{-1}$: 3300 (NH), 1760, 1610 (C=O), 1180, 1060 (C—O).

EXAMPLE 18

40 mg of 2,3,5,10,11,11a-hexahydro-11-ethoxy-9-hydroxy-8-methyl-1H-pyrrolo[2,1-C][1,4]benzodiazepin-5-one was treated in the same manner as in Example 17. Thus, 23 mg of 2,3,5,10,11,11a-hexahydro-9-acetoxy-11-ethoxy-8-methyl-1H-pyrrolo[2,1-C][1,4]benzodiazepin-5-one was obtained as a colorless crystal having a melting point of 145° to 147° C.

Anal. calcd. for $C_{17}H_{22}N_2O_4$: C 64.13, H 6.97, N 8.80. Found: C 63.95, H 6.95, N 8.97.

IR $\nu_{max}^{Nujol}$ cm$^{-1}$: 3300 (NH), 1770, 1610 (C=O), 1180, 1070 (C—O).

EXAMPLE 19

50 mg of 2,3,5,11a-tetrahydro-9-hydroxy-8-methyl-1H-pyrrolo[2,1-C][1,4]benzodiazepin-5-one was treated in the same manner as in Example 17. Thus, 24 mg of 2,3,5,11a-tetrahydro-9-acetoxy-8-methyl-1H-pyrrolo[2,1-C][1,4]benzodiazepin-5-one was obtained as a light yellow powdery product. The product had a melting point of 142° to 145° C.

Anal. calcd. for $C_{15}H_{16}N_2O_3$: C 66.16, H 5.92, N 10.29. Found: C 66.33, H 5.91, N 10.14.

IR $\nu_{max}^{Nujol}$ cm$^{-1}$: 1765, 1615 (C=O).

EXAMPLE 20

20 mg of 2,3,5,10,11,11a-hexahydro-9-acetoxy-11-methoxy-8-methyl-1H-pyrrolo[2,1-C][1,4]benzodiazepin-5-one was treated in the same manner as in Example 8. Thus, 13 mg of 2,3,5,11a-tetrahydro-9-acetoxy-8-methyl-1H-pyrrolo[2,1-C][1,4]benzodiazepin-5-one was obtained as a light yellow powdery product having a melting point of 141° to 144.5° C. The infrared absorption spectrum of this product just coincided with that of the compound obtained in Example 19.

EXAMPLE 21

10 mg of 2,3,5,11a-tetrahydro-9-acetoxy-8-methyl-1H-pyrrolo[2,1-C][1,4]benzodiazepin-5-one was treated in the same manner as in Example 11. Thus, 6 mg of 2,3,5,10,11,11a-hexahydro-9-acetoxy-11-methoxy-8-methyl-1H-pyrrolo[2,1-C][1,4]benzodiazepin-5-one was obtained as a light yellow needle-like crystal having a melting point of 146° to 149° C. Its infrared absorption spectrum just coincided with that of the product of Example 17.

EXAMPLE 22

30 mg of 2,3,5,11a-tetrahydro-9-acetoxy-8-methyl-1H-pyrrolo[2,1-C][1,4]benzodiazepin-5-one was treated in the same manner as in Example 12. Thus, 24 mg of 2,3,5,10,11,11a-hexahydro-9-acetoxy-11-hydroxy-8-methyl-1H-pyrrolo[2,1-C][1,4]benzodiazepin-5-one was obtained as a yellow-colored crystal having a melting point of 142° to 145° C.

Anal. calcd. for $C_{15}H_{18}N_2O_4$: C 62.06, H 6.25, N 9.65. Found: C 63.25, H 6.23, N 9.41.

IR $\nu_{max}^{Nujol}$ cm$^{-1}$: 3340 (NH), 1760, 1610 (C=O), 1170, 1070 (C—O).

EXAMPLE 23

40 mg of 2,3,5,11a-tetrahydro-9-acetoxy-1H-pyrrolo[2,1-C][1,4]benzodiazepin-5-one was treated in the same manner as in Example 12. Thus, 31 mg of 2,3,5,10,11,11a-hexahydro-9-acetoxy-11-hydroxy-1H-pyrrolo[2,1-C][1,4]-benzodiazepin-5-one was obtained as a yellow-colored crystal having a melting point of 143° to 145° C.

Anal. calcd. for $C_{14}H_{16}N_2O_4$: C 60.86, H 5.84, N 10.14. Found: C 60.59, H 5.92, N 10.26.

IR $\nu_{max}^{Nujol}$ cm$^{-1}$: 3330 (NH), 1760, 1605 (C=O), 1180, 1070 (C—O).

EXAMPLE 24

40 mg of 2,3,5,10,11,11a-hexahydro-9-hydroxy-11-methoxy-1H-pyrrolo[2,1-C][1,4]benzodiazepin-5-one was treated in the same manner as in Example 17. Thus, 23 mg of 2,3,5,10,11,11a-hexahydro-9-acetoxy-11-methoxy-1H-pyrrolo[2,1-C][1,4]benzodiazepin-5-one was obtained as a light yellow needle-like crystal having a melting point of 147° to 150° C.

IR $\nu_{max}^{Nujol}$ cm$^{-1}$: 3320 (NH), 1760, 1610 (C=O), 1190, 1070 (C—O).

EXAMPLE 25

300 mg of 6,8,9,10,10a,11-hexahydro-1-phenyl-1H-oxazolo[5,4,3-jk]pyrrolo[2,1-C][1,4]benzodiazepin-6,11-dione was treated in the same manner as in Example 7. Thus, 78 mg of 2,3,5,10,11,11a-hexahydro-11-ethoxy-9- hydroxy-1H-pyrrolo[2,1-C][1,4]benzodiazepin-5-one was obtained in a colorless crystalline form. Recrystallization of the resulting product from ethanol gave a colorless needle-like crystal having a melting point of 153° to 155° C.

Anal. calcd. for $C_{14}H_{18}N_2O_3$: C 64.11, H 6.92, N 18.30. Found: C 63.98, H 6.95, N 18.47.

IR $\nu_{max}^{Nujol}$ cm$^{-1}$: 3250 (OH, NH), 1600 (C=O), 1185, 1060 (C—O).

EXAMPLE 26

36 mg of 2,3,5,10,11,11a-hexahydro-11-ethoxy-9-hydroxy-1H-pyrrolo[2,1-C][1,4]benzodiazepin-5-one was treated in the same manner as in Example 17. Thus, 20 mg of 2,3,5,10,11,11a-hexahydro-9-acetoxy-11-ethoxy-1H-pyrrolo[2,1-C][1,4]benzodiazepin-5-one was obtained as a colorless crystal having a melting point of 146° to 149° C.

IR $\nu_{max}^{Nujol}$ cm$^{-1}$: 3300 (NH), 1765, 1610 (C=O), 1180, 1060 (C—O).

EXAMPLE 27

45 mg of 2,3,5,11a-tetrahydro-9-acetoxy-8-methoxy-1H-pyrrolo[2,1-C][1,4]benzodiazepin-5-one was treated in the same manner as in Example 12. Thus, 33 mg of 2,3,5,10,11,11a-hexahydro-9-acetoxy-11-hydroxy-8-methoxy-1H-pyrrolo[2,1-C][1,4]benzodiazepin-5-one was obtained as a yellow-colored crystal having a melting point of 144° to 146° C.

Anal. calcd. for $C_{15}H_{18}N_2O_5$: C 58.82, H 5.92, N 9.15. Found: C 59.08, H 5.90, N 9.01.

IR $\nu_{max}^{Nujol}$ cm$^{-1}$: 3340 (NH, OH), 1770, 1610 (C=O), 1180, 1080 (C—O).

EXAMPLE 28

40 mg of 2,3,5,10,11,11a-hexahydro-8,11-dimethoxy-9-hydroxy-1H-pyrrolo[2,1-C][1,4]benzodiazepin-5-one was treated in the same manner as in Example 17. Thus, 25 mg of 2,3,5,10,11,11a-hexahydro-9-acetoxy-8,11-dimethoxy-1H-pyrrolo[2,1-C][1,4]benzodiazepin-5-one was obtained as a colorless crystal having a melting point of 143° to 145° C.

IR $\nu_{max}^{Nujol}$ cm$^{-1}$: 3300 (NH), 1760, 1610 (C=O), 1180, 1070 (C—O).

EXAMPLE 29

350 mg of 6,8,9,10,10a,11-hexahydro-3-methoxy-1-phenyl-1H-oxazolo[5,4,3-jk]pyrrolo[2,1-C][1,4]benzodiazepin-6,11-dione was treated in the same manner as in Example 7. Thus, 80 mg of 2,3,5,10,11,11a-hexahydro-11-ethoxy-9-hydroxy-8-methoxy-1H-pyrrolo[2,1-C][1,4]benzodiazepin-5-one was obtained as a colorless needle-like crystal having a melting point of 155° to 158° C.

Anal. calcd. for $C_{15}H_{20}N_2O_4$: C 61.63, H 6.90, N 9.58. Found: C 61.48, H 6.95, N 9.78.

IR $\nu_{max}^{Nujol}$ cm$^{-1}$: 3200 (NH, OH), 1605 (C=O), 1190, 1060 (C—O).

EXAMPLE 30

40 mg of 2,3,5,10,11,11a-hexahydro-11-ethoxy-9-hydroxy-8-methoxy-1H-pyrrolo[2,1-C][1,4]benzodiazepin-5-one was treated in the same manner as in Example 17. Thus, 25 mg of 2,3,5,10,11,11a-hexahydro-9-acetoxy-11-ethoxy-8-methoxy-1H-pyrrolo[2,1-C][1,4]benzodiazepin-5-one was obtained as a colorless crystal having a melting point of 143° to 146° C.

IR $\nu_{max}^{Nujol}$ cm$^{-1}$: 3300 (NH), 1765, 1605 (C=O), 1180, 1070 (C—O).

EXAMPLE 31

40 mg of 2,3,5,11a-tetrahydro-9-hydroxy-1H-pyrrolo[2,1-C][1,4]benzodiazepin-5-one was treated in the same manner as in Example 17. Thus, 20 mg of 2,3,5,11a-tetrahydro-9-acetoxy-1H-pyrrolo[2,1-C][1,4]benzodiazepin-5-one was obtained as a light yellow powdery product. The product had a melting point of 143° to 146° C.

Anal. calcd. for $C_{14}H_{14}N_2O_3$: C 65.11, H 5.46, N 10.85. Found: C 65.40, H 5.38, N 10.68.

IR $\nu_{max}^{Nujol}$ cm$^{-1}$: 1765, 1610 (C=O).

EXAMPLE 32

42 mg of 2,3,5,11a-tetrahydro-9-hydroxy-8-methoxy-1-H-pyrrolo[2,1-C][1,4]benzodiazepin-5-one was treated in the same manner as in Example 17. Thus, 21 mg of 2,3,5,11a-tetrahydro-9-acetoxy-8-methoxy-1H-pyrrolo[2,1-C][1,4]benzodiazepin-5-one was obtained as a light yellow powdery product having a melting point of 144° to 146° C.

Anal. calcd. for $C_{15}H_{15}N_2O_4$: C 62.49, H 5.59, N 9.72. Found: C 62.31, H 5.62, N 10.01.

IR $\nu_{max}^{Nujol}$ cm$^{-1}$: 1765, 1620 (C=O).

EXAMPLE 33

10 mg of 2,3,5,11a-tetrahydro-9-acetoxy-1H-pyrrolo[2,1-C][1,4]benzodiazepin-5-one was treated in the same manner as in Example 11. Thus, 5 mg of 2,3,5,10,11,11a-hexahydro-9-acetoxy-11-methoxy-1H-pyrrolo[2,1-C][1,4]benzodiazepin-5-one was obtained as a light yellow needle-like crystal having a melting point of 148° to 150° C. Its infrared absorption spectrum just coincided with that of the product of Example 24.

What is claimed is:

1. A compound represented by the following formula:

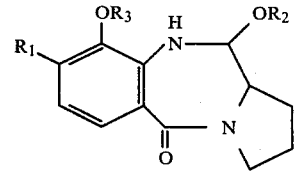

wherein $R_1$ represents hydrogen atom, methyl group, hydroxy group or methoxy group; $R_2$ represents hydrogen atom, methyl group, ethyl group or phenyl-(lower alkyl) group; and $R_3$ represents hydrogen atom or acetyl group.

2. 2,3,5,10,11,11a-hexahydro-9-hydroxy-11-methoxy-8-methyl-1H-pyrrolo[2,1-C][1,4]benzodiazepin-5-one.

3. 2,3,5,10,11,11a-hexahydro-11-ethoxy-9-hydroxy-8-methyl-1H-pyrrolo[2,1-C][1,4]benzodiazepin-5-one.

4. 2,3,5,10,11,11a-hexahydro-9-hydroxy-11-methoxy-1H-pyrrolo[2,1-C][1,4]benzodiazepin-5-one.

5. 2,3,5,10,11,11a-hexahydro-8,11-dimethoxy-9-hydroxy-1H-pyrrolo[2,1-C][1,4]benzodiazepin-5-one.

6. 2,3,5,10,11,11a-hexahydro-9,11-dihydroxy-8-methyl-1-H-pyrrolo[2,1-C][1,4]benzodiazepin5-one.

7. 2,3,5,10,11,11a-hexahydro-9,11-dihydroxy-1H-pyrrolo[2,1-C][1,4]benzodiazepin-5-one.

8. 2,3,5,10,11,11a-hexahydro-9,11-dihydroxy-8-methoxy-1H-pyrrolo[2,1-C][1,4]benzodiazepin-5-one.

9. 2,3,5,10,11,11a-hexahydro-9-acetoxy-11-methoxy-8-methyl-1H-pyrrolo[2,1-C][1,4]benzodiazepin-5-one.

10. 2,3,5,10,11,11a-hexahydro-9-acetoxy-11-ethoxy-8-methyl-1H-pyrrolo[2,1-C][1,4]benzodiazepin-5-one.

11. 2,3,5,10,11,11a-hexahydro-9-acetoxy-11-hydroxy-8-methyl-1H-pyrrolo[2,1-C][1,4]benzodiazepin-5-one.

12. 2,3,5,10,11,11a-hexahydro-9-acetoxy-11-hydroxy-1H-pyrrolo[2,1-C][1,4]benzodiazepin-5-one.

13. 2,3,5,10,11,11a-hexahydro-9-acetoxy-11-methoxy-1H-pyrrolo[2,1-C][1,4]benzodiazepin-5-one.

14. 2,3,5,10,11,11a-hexahydro-11-ethoxy-9-hydroxy-1H-pyrrolo[2,1-C][1,4]benzodiazepin-5-one.

15. 2,3,5,10,11,11a-hexahydro-9-acetoxy-11-ethoxy-1H-pyrrolo[2,1-C][1,4]benzodiazepin-5-one.

16. 2,3,5,10,11,11a-hexahydro-9-acetoxy-11-hydroxy-8-methoxy-1H-pyrrolo[2,1-C][1,4]benzodiazepin-5-one.

17. 2,3,5,10,11,11a-hexahydro-9-acetoxy-8,11-dimethoxy-1H-pyrrolo[2,1-C][1,4]benzodiazepin-5-one.

18. 2,3,5,10,11,11a-hexahydro-11-ethoxy-9-hydroxy-8-methoxy-1H-pyrrolo[2,1-C][1,4]benzodiazepin-5-one.

19. 2,3,5,10,11,11a-hexahydro-9-acetoxy-11-ethoxy-8-methoxy-1H-pyrrolo[2,1-C][1,4]benzodiazepin-5-one.

20. A compound according to claim 1 wherein $R_3$ is acetyl.

* * * * *